(12) United States Patent
Viola

(10) Patent No.: US 7,833,200 B2
(45) Date of Patent: Nov. 16, 2010

(54) TROCAR ASSEMBLY WITH RADIALLY MOVEABLE HOUSING

(75) Inventor: Frank J. Viola, Sandy Hook, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

(21) Appl. No.: 12/467,390

(22) Filed: May 18, 2009

(65) Prior Publication Data
US 2009/0326464 A1 Dec. 31, 2009

Related U.S. Application Data

(60) Provisional application No. 61/076,188, filed on Jun. 27, 2008.

(51) Int. Cl.
*A61M 5/178* (2006.01)
(52) U.S. Cl. .............................. 604/167.06
(58) Field of Classification Search .......... 604/158, 604/162, 164.04, 164.309, 164.01, 164.11, 604/165.01, 165.02, 164.07, 192, 165.04, 604/167.01, 167.06, 117, 23, 24, 26; 606/108
See application file for complete search history.

(56) References Cited

U.S. PATENT DOCUMENTS

| 5,215,531 | A | | 6/1993 | Maxson et al. |
|---|---|---|---|---|
| 5,232,451 | A | * | 8/1993 | Freitas et al. ............ 604/174 |
| 5,350,362 | A | * | 9/1994 | Stouder, Jr. ............ 604/167.03 |
| 5,385,553 | A | | 1/1995 | Hart et al. |
| 6,162,196 | A | | 12/2000 | Hart et al. |
| 7,011,314 | B2 | | 3/2006 | McFarlane |
| 7,083,626 | B2 | | 8/2006 | Hart et al. |
| 7,217,277 | B2 | | 5/2007 | Parihar et al. |
| 7,470,255 | B2 | | 12/2008 | Stearns et al. |
| 2003/0139756 | A1 | | 7/2003 | Brustad |
| 2006/0211992 | A1 | | 9/2006 | Prosek |
| 2007/0004968 | A1 | | 1/2007 | Bonadio et al. |
| 2007/0210018 | A1 | | 9/2007 | Wallwiener et al. |
| 2008/0051739 | A1 | | 2/2008 | McFarlane |
| 2008/0125716 | A1 | | 5/2008 | Cruz |

FOREIGN PATENT DOCUMENTS

| EP | 0513962 | 11/1992 |
|---|---|---|
| WO | WO 02/41795 | 5/2002 |

OTHER PUBLICATIONS

European Search Report for corresponding EP 09251619 date of mailing is Oct. 19, 2009 (3 pages).

* cited by examiner

*Primary Examiner*—Nicholas D Lucchesi
*Assistant Examiner*—Christopher D Koharski

(57) ABSTRACT

A surgical access assembly includes a cannula, a housing mounted to the cannula, and a seal disposed within the cannula. The cannula is adapted for insertion through tissue to permit access to an underlying tissue site. The cannula defines a longitudinal axis and has a longitudinal passageway for passage of a surgical object for positioning with respect to the tissue site. The housing is adapted for movement relative to the cannula in a direction transverse to the longitudinal axis. The seal has a passage for reception of the surgical object in substantial sealed relation therewith. The access assembly may further include a support member mounted to the cannula. The support member adapted to maintain a predetermined distance between the housing and the tissue. The support member may be securely affixed to, or selectively positionable along, the cannula with respect to the longitudinal axis.

16 Claims, 5 Drawing Sheets

TROCAR ASSEMBLY WITH RADIALLY MOVEABLE HOUSING

CROSS REFERENCE TO RELATED APPLICATION

The present application claims the benefit of and priority to U.S. Provisional Application Ser. No. 61/076,188, filed on Jun. 27, 2008, the entire contents of which are incorporated herein by reference.

BACKGROUND

1. Technical Field

The present disclosure relates generally to trocar assemblies for accessing the body, and more particularly, to a trocar assembly including a housing that may laterally translate about the proximal end of a cannula.

2. Background of Related Art

Trocars and other access assemblies are used by surgeons to operate on a patient without having to create large incisions that may become infected and may cause major scaring. Trocar assemblies are known in the art, as are the instruments inserted therethrough for operating within the body cavity. Typically a trocar assembly comprises two major components, a sleeve including a housing and a cannula, and an obturator. The housing may be securely affixed to the cannula, or the housing may instead be adjustable. Typically, a trocar system having an adjustable or floating housing includes a housing configured to permit lateral movement of the housing relative to the cannula. By incorporating a floating housing into the trocar assembly an instrument inserted through the housing may be manipulated with a greater degree of control and without moving the cannula.

In order to provide a greater space in which a surgeon may operate and to increase visibility of the tissue being operated on, the body cavity is generally insufflated. To avoid gas leakage from within the cavity prior to or during insertion of an instrument through the cannula, and as instruments are being removed and replace, various seal members have been developed. Conventional trocar assemblies having a floating housing include at least one seal member fixedly disposed within the housing. Thus, as an instrument is inserted through a trocar assembly, a seal is created about the instrument as it passes through the housing. In this manner, when the housing, or the instrument inserted therethrough, is manipulated the seal member and the housing are moved together. By including the seal member within the housing the connection between the housing and the cannula must be air-tight to prevent the leakage of insufflation gas. Frequent or repeated use of the trocar assembly may compromise the integrity of the connection between the housing and the cannula. This wear on the connection may result in malfunction of the seal and result in leakage of the insufflation gas.

Additionally, the location of the seal member within the access assembly affects the handling of an instrument passing therethrough. The seal member in effect creates a pivot point around which the instrument may be manipulated. The closer the pivot point is to the target site, the greater the degree of control a surgeon may have while manipulating the instrument inserted therethrough. By including the seal within the housing the pivot point is as far from the target site as possible, thereby reducing the degree of control the surgeon has over the instrument.

Therefore, it would be beneficial to have a trocar assembly including a floating housing wherein the instrument seal is located distally of the floating housing or within the cannula.

SUMMARY

According to an aspect of the present disclosure, a surgical access assembly is provided. The access assembly includes a cannula adapted for insertion through tissue to permit access to an underlying tissue site. The cannula defines a longitudinal axis and has a longitudinal passageway for passage of a surgical object for positioning with respect to the tissue site. The access assembly also includes a housing mounted to the cannula. The housing is adapted for movement relative to the cannula in a direction transverse to the longitudinal axis. The access assembly further includes a seal disposed within the cannula and has a passage for reception of the surgical object in substantial sealed relation therewith.

The surgical access assembly may further include a support member mounted to the cannula. The support member is adapted to maintain a predetermined distance between the housing and the tissue. The support member may be securely affixed to the cannula. The support member may instead be selectively positionable along the cannula with respect to the longitudinal axis.

The surgical access assembly may include a means for maintaining the support member at a selected position along the longitudinal axis. The cannula and the support member may include threaded portions adapted to cooperate to selectively position the support member along the cannula.

The support member may be adapted for rotational movement relative to the housing between a first position corresponding to a secured position of the housing with respect to the cannula whereby the housing is prevented from moving in the direction transverse to the longitudinal axis, and a second position corresponding to a release position of the housing with respect to the cannula whereby the housing is permitted to move in the direction transverse to the longitudinal axis.

The housing may further include a seal disposed across the longitudinal opening. The surgical access assembly may further include a compressible ring mounted between the cannula and the housing for maintaining the housing relative to the cannula. The compressible ring may be constructed of rubber or foam.

BRIEF DESCRIPTION OF THE DRAWINGS

The foregoing summary, as well as the following detailed description will be better understood when read in conjunction with the appended figures. For the purpose of illustrating the present disclosure, a preferred embodiment is shown. It is understood, however, that the present disclosure is not limited to the precise arrangement and instrumentalities shown.

DESCRIPTION OF THE EMBODIMENTS

Figure 1:
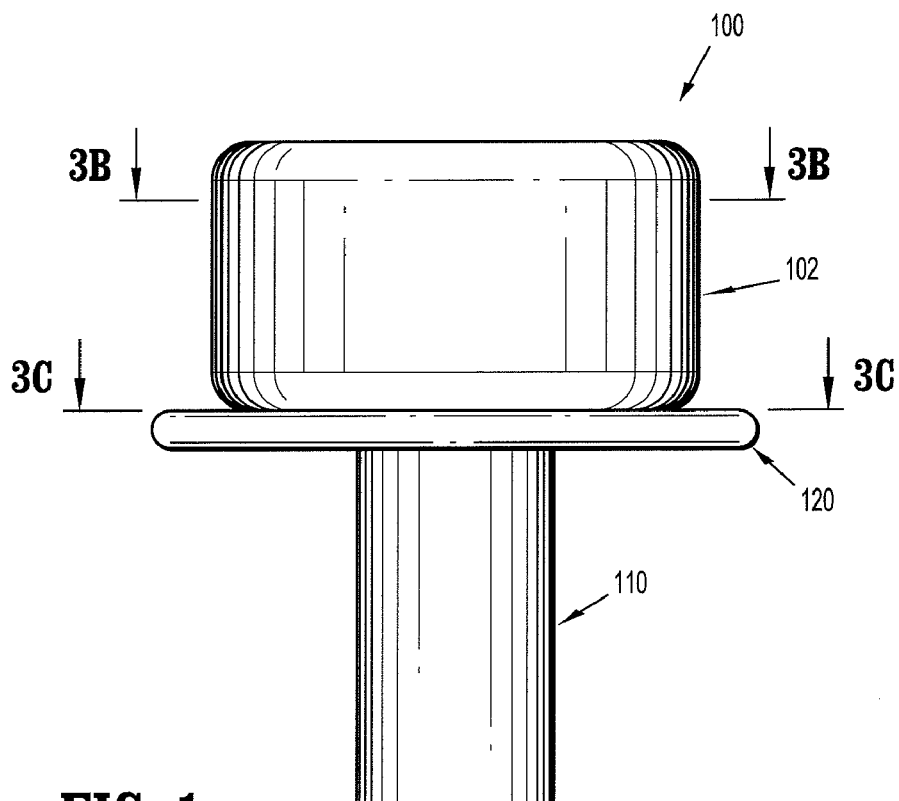
FIG. 1 is a side plan view of a trocar assembly according an embodiment of the present disclosure.

Referring now to the drawings wherein like reference numerals illustrate similar components throughout the several views. As shown in the drawings and as described throughout the following description, as is traditional when referring to relative positioning on an object, the term "proximal" refers to the end of the apparatus which is closer to the user and the term "distal" refers to the end of the apparatus which is further from the user.

FIGS. 1-5B illustrate a trocar assembly 100 in accordance with the principles of the present disclosure. Referring initially to FIG. 1, trocar assembly 100 includes a housing 102 configured to receive a proximal end 110a of a cannula 110. As will be discussed below, housing 102 is configured to move or float relative to cannula 110 in a plane perpendicular to cannula 110, thereby permitting cooperating or at least lateral movement of an instrument E (FIG. 4A) extending therethrough. Trocar assembly 100 further includes a support member 120 secured to cannula 110 and configured for supporting housing 102 as it is maintained relative to cannula 110. Trocar assembly 100 may be configured for use with any known endoscopic or laparoscopic instrument.

Figure 2:
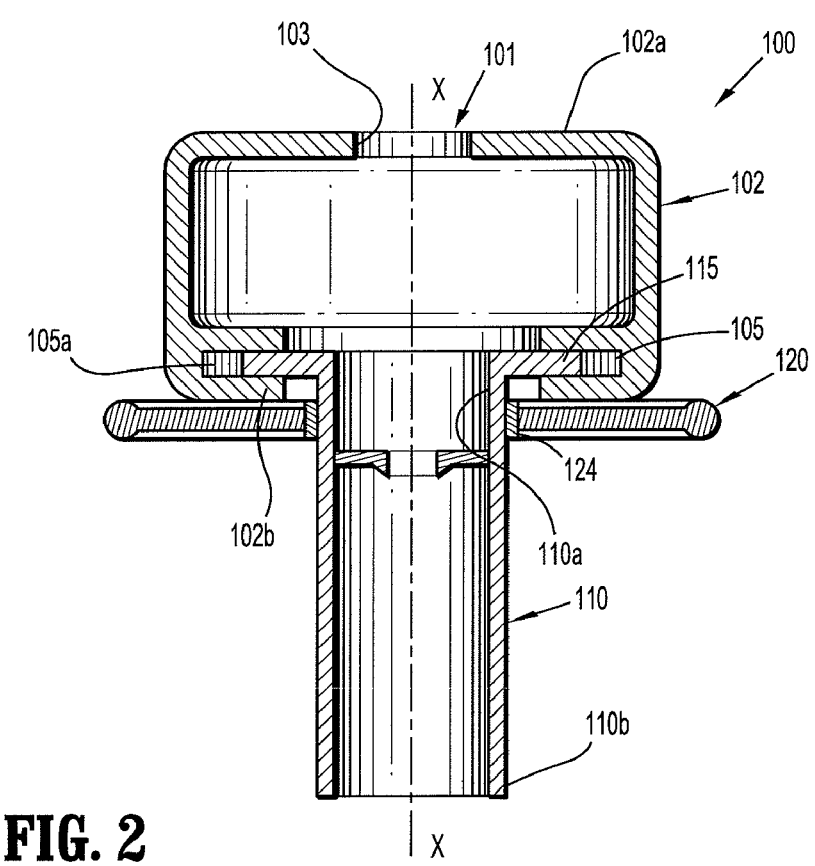
FIG. 2 is a side cross-sectional view of the trocar assembly of FIG. 1.
Figure 4A:
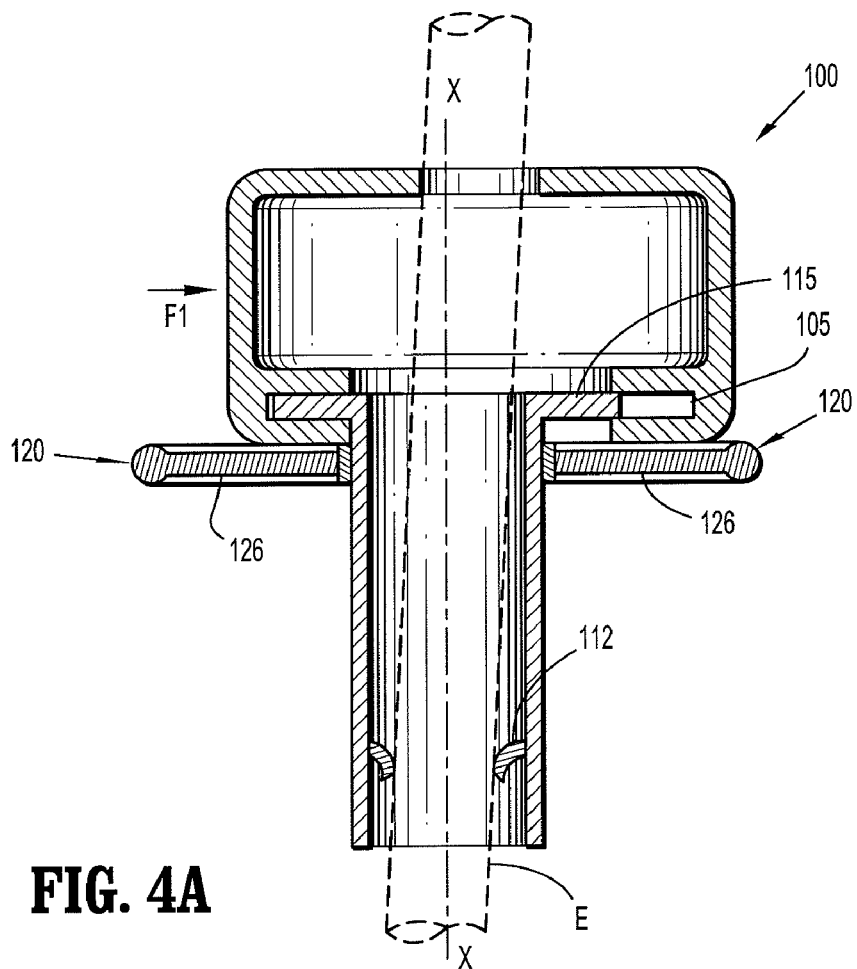
FIG. 4A is a cross-sectional side view of the trocar assembly of FIGS. 1-3C, in a first shifted condition.

Turning now to FIG. 2, housing 102 forms a substantially annular member having a partially closed proximal end 102a and a partially closed distal end 102b. Housing 102 may instead define an oval, square, rectangular or other suitable profile. Housing 102 may be constructed of metal, plastic, polymer or other suitable material. Housing 102 defines a passageway 101 therethrough for receiving an instrument E (FIG. 4A). Proximal end 102a of housing 102 defines an opening 103 configured to receive instrument E therethrough.

Although not necessary for proper operation of trocar assembly 100, opening 103 may include a seal (not shown) for receiving instrument E therethrough. In this manner, housing 102 may further include a port (not shown) configured to fluidly communicate with a source of insufflation gas (not shown). Opening 103 may be configured to receive instruments of various diameters and configurations. In an alternate embodiment, proximal end 102a of housing 102 may be configured with tabs or latches (not shown) for selectively securing an instrument (not shown) to housing 102, thereby permitting greater control during manipulation.

Still referring to FIG. 2, distal end 102b of housing 102 defines a horizontal slot 105 for receiving a flange 115 formed on proximal end 110a of cannula 110. As will be discussed in further detail below, distal end 102b of housing 102 is configured to floatingly receive flange 105 therein. A rubber or foam ring 105a may be included with slot 105. In the event that housing 102 is pressurized, foam ring 105a may form a seal between the connection of housing 102 and cannula 110 to prevent leakage of the insufflation gas.

With reference still to FIG. 2, cannula 110 is configured to be inserted through the skin into a body cavity with the aid of an obturator (not shown) or may instead include a blade or piercing tip for penetrating through the skin and into a body cavity. Cannula 110 forms a substantially tubular member having proximal and distal ends 110a, 110b. Cannula 110 may be composed of plastic, metal, polymers or the like. Cannula 110 may be disposable, or in the alternative, reusable. Cannula 110 may be rigid, or alternatively, cannula 110 may be flexible. As described above, proximal end 110b of cannula 110 includes a flange 115. Flange 115 is configured to float or move relative to housing 102 within slot 105 formed in distal end 102b thereof. Distal end 110b of cannula 110 may be open. Distal end 110b may instead be configured to include one or more seal members (not shown).

Cannula 110 includes at least one valve or seal member 112 along the length thereof for receiving an instrument E (FIG. 4A) therethrough. Seal member 112 defines an opening 112a for receiving instrument E therethrough. Opening 112a may be sized to receive instruments of any diameter and configuration. In an alternate embodiment, cannula 110 may include a port (not shown) for fluidly communication trocar assembly 100 with a source on insufflation gas.

Figure 3A:
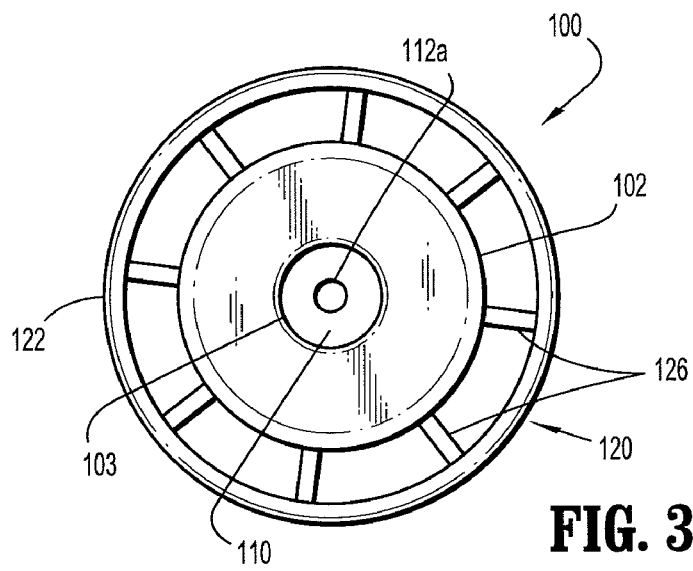
FIG. 3A is a top view of the trocar assembly of FIGS. 1 and 2.
Figure 3B:
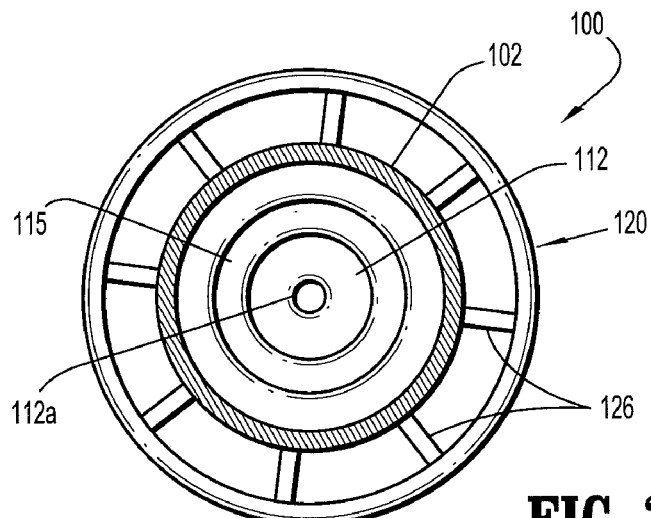
FIG. 3B is a cross-sectional view of the trocar assembly of FIG. 1 taken along line 3B-3B of FIG. 1.
Figure 3C:
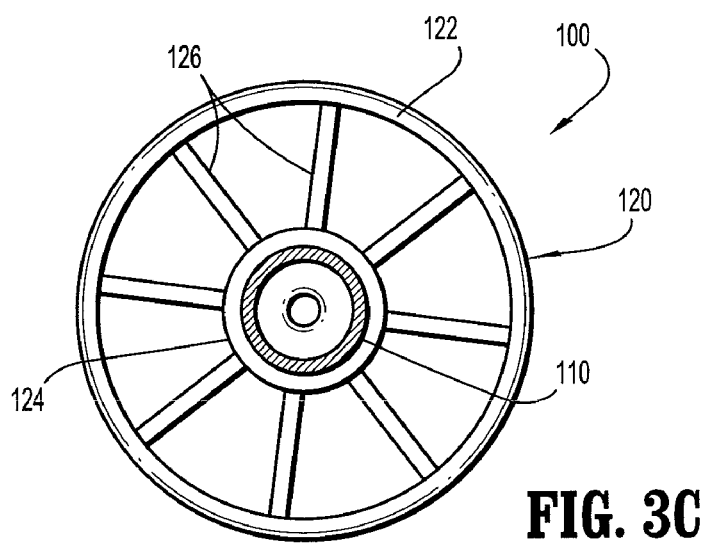
FIG. 3C is a cross-sectional view of the trocar assembly of FIG. 1 taken along line 3C-3C of FIG. 1.

Referring now to FIGS. 3A-3C, trocar assembly 100 includes a support member 120 securely affixed to proximal end 110a of cannula 110 for supporting housing 102 as housing 102 is moved relative to cannula 110. Support member 120 includes a substantially wheel shaped member including an outer rim 122, an inner rim 124, and spindles 126 extending therebetween. Referring back to FIG. 2, inner rim 124 of support member 120 is securely affixed to proximal end 110a of cannula 110. Support member 120 may be affixed to cannula 110 using adhesive, mechanical fasteners, friction fit, threaded members or any other suitable means. Support member 120 is positioned about cannula 110 such that distal end 102b of housing 102 rests on spindles 126. Outer rim 122 is configured to have a diameter larger than that of housing 102. By positioning larger support member 120 about cannula 110 in contact with housing 102 adjustable positioned on proximal end 110a, housing 102 is retained in a horizontal position as housing 102 is adjusted relative to cannula 110. Spindles 120 and/or the portion of housing 102 that contacts spindles 120 may include a coating of a friction reducing material, such as Teflon® to promote movement of housing 102 relative to cannula 110.

Figure 6A:
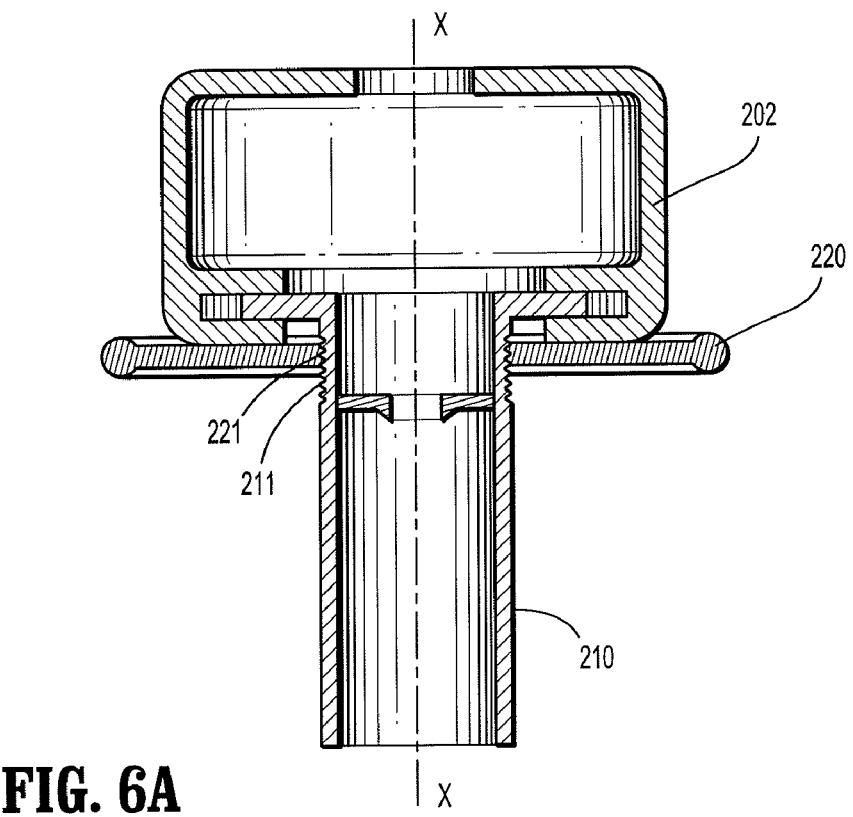
FIG. 6A is a cross-sectional side view of a trocar assembly according to an alternate embodiment of the present disclosure, with the housing shown in a first or locked position.
Figure 6B:
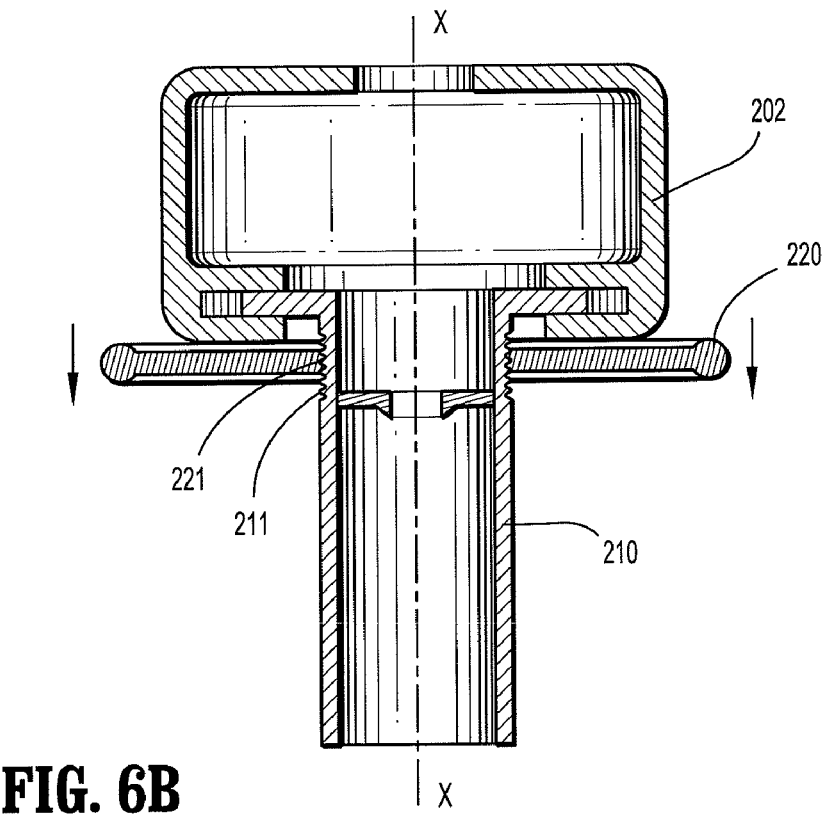
FIG. 6B is a cross-sectional side vie of the trocar assembly of FIG. 6A, with the housing shown in a second or adjustable position.

Turning now to FIGS. 6A and 6B, in an alternative embodiment, support member 220 may be configured to selectively secure housing 202 in position relative to cannula 210. In this manner, housing 202 would be locked in position relative to housing 202 until an action by the user disengages housing 202 from cannula 210. Housing 202 may be locked relative to cannula 210 with mechanical fasteners (not shown) or instead support 220 may be configured, as shown, to longitudinally translate along cannula 210, thereby permitting engagement of support 220 with housing 202. By engaging housing 202 (FIG. 6A) support 220 prevents movement thereof. As shown, cannula 210 and support member 220 may include threads 211, 221, respectively. Threads 211, 221 may be of any size and include any configuration. Rotation of support member 220 relative to cannula 210 advances support member 220 distally along cannula 220 into housing 202. The engagement of support member 220 with housing 202 prevents the lateral translation of housing 202. Rotation of support member 220 in an opposite direction about cannula 210 may disengage support member 220 from housing 202, thereby permitting movement of housing 202 relative to cannula 210 (FIG. 6B). It is also envisioned that the threaded arrangement may enable the clinician to position support member 220 at selected or predetermined positions along cannula 210 and with respect to the longitudinal axis. Thus, support member 220 may space housing 202 at predetermined locations relative to the tissue.

Turning back to FIGS. 1-5B, in operation, trocar assembly 100 is initially inserted into a body cavity in a manner similar to known trocar assemblies. As discussed above, distal end 110b of cannula 110 may be configured to pierce through the skin and into the body cavity or an obturator (not shown) may be inserted through trocar assembly 100 to assist in the piercing of the skin and the creation of an opening for cannula 110 to be received through. Once received in the body cavity, the obturator, if used, may be removed, and trocar assembly 100 is ready to receive an instrument.

Referring initially to FIG. 2, in a first or initial position housing 102 and cannula 110 are concentric with one another and define a central axis x-x. As discussed above, foam or rubber ring 105a may be received within slot 105 formed in distal end 102b of housing 102 to maintain housing 102 in this first or initial position concentric with cannula 110.

Referring now to FIGS. 4A-5B, trocar assembly 100 is configured to receive an instrument E through housing 102 and cannula 110 and into a body cavity (not shown). Instrument E is typically received through housing 102 and cannula 110 when trocar assembly 100 is in a first or initially position (FIG. 2), with housing 102 and cannula 110 concentric with one another. However, instrument E may be received within trocar assembly 100 when housing 102 is non-concentric or in shifted position relative to cannula 110.

Figure 4B:
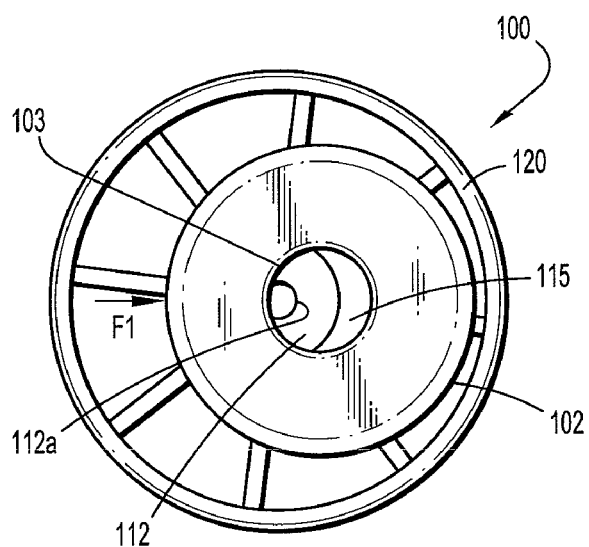
FIG. 4B is a top view of the trocar assembly of FIG. 4A.
Figure 5A:
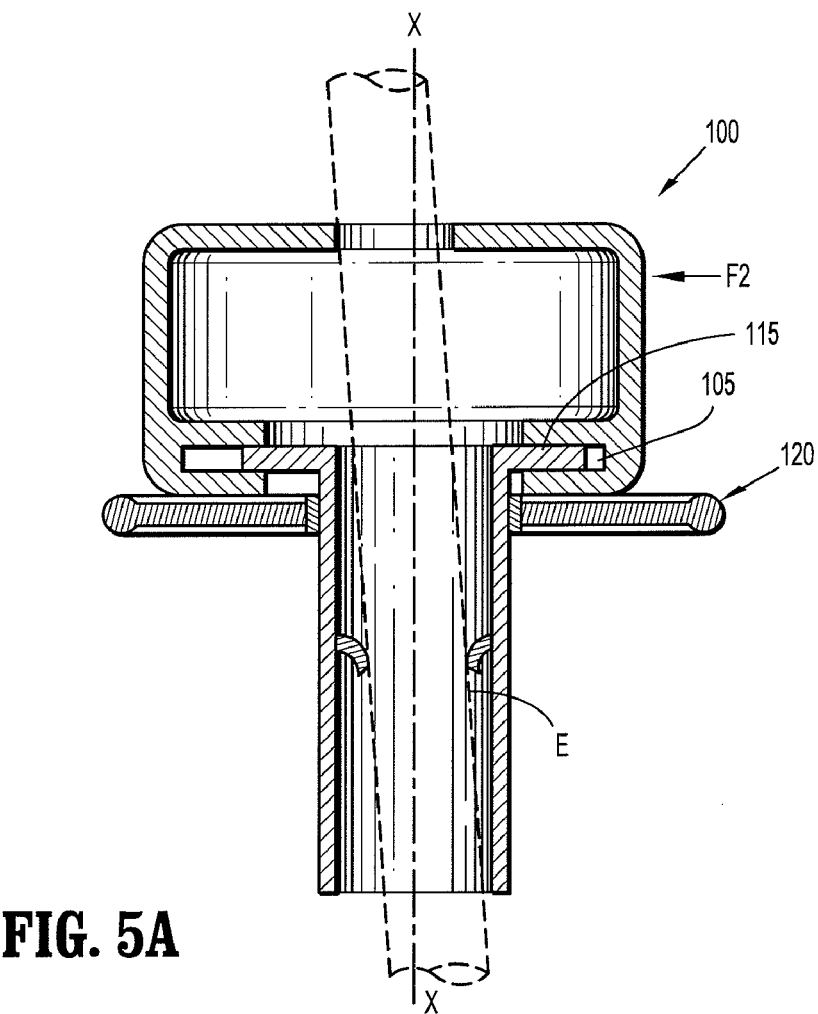
FIG. 5A is a cross-sectional side view of the trocar assembly of FIGS. 1-4B, in a second shifted condition.
Figure 5B:
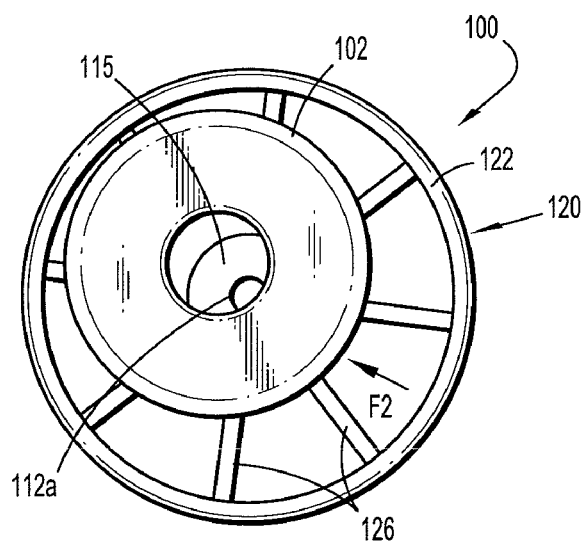
FIG. 5B is a top view of the trocar assembly of FIG. 4A.

Referring initially to FIGS. 4A and 4B, when a user applies a lateral force against housing 102 in a direction indicated by arrow F1, housing 102 translates horizontally relative to cannula 110 in the direction force F1. Slot 105 formed in distal end 102b of housing 102 permits this movement of housing 102 relative to cannula 110. In this manner, housing 102 and thus, instrument E inserted therethrough, may be manipulated relative to cannula 110 without moving cannula 110. Referring now to FIGS. 5A and 5B, application of a lateral force in a second direction, indicated by arrow F2, causes housing 102 to translate horizontally relative to cannula 110 in the direction of force F2. As discussed above, slot 105 may include a rubber or foam ring 105a that may compress as housing 102 is moved about cannula 110. The release of force F1, F2 against housing 102 causes ring 105a to decompress, thereby returning housing 102 it its initial, concentric position with cannula 110. In this manner, housing 102 may be moved any direction in a horizontal plane relative to cannula 110. By being able to laterally move housing 102 relative to cannula 110, a user may more precisely manipulate and have greater control over instrument E inserted therethrough.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims append hereto.

What is claimed is:

1. A surgical access assembly, which comprises:
   a cannula adapted for insertion through tissue to permit access to an underlying tissue site, the cannula defining a longitudinal axis and having a longitudinal passageway for passage of a surgical object for positioning with respect to the tissue site;
   a housing mounted to the cannula, the housing adapted for movement relative to the cannula in a direction transverse to the longitudinal axis;
   a seal disposed within the cannula and having a passage for reception of the surgical object in substantial sealed relation therewith; and
   a support member mounted adjacent the housing, the support member adapted for movement relative to the housing between a first position corresponding to a secured position of the housing with respect to the cannula whereby the housing is prevented from moving in the direction transverse to the longitudinal axis, and a second position corresponding to a release position of the housing with respect to the cannula whereby the housing is permitted to move in the direction transverse to the longitudinal axis.

2. The surgical access assembly according to claim 1 wherein the support member is mounted to the cannula, the support member adapted to maintain a predetermined distance between the housing and the tissue.

3. The surgical access assembly according to claim 1 wherein the support member is mounted to the cannula and is selectively longitudinally positionable along the cannula with respect to the longitudinal axis to move between the first and second positions of the support member.

4. The surgical access assembly according to claim 3 including means for maintaining the support member at either the first position or the second position along the longitudinal axis.

5. The surgical access assembly according to claim 3 wherein the cannula and the support member include threaded portions dimensioned and adapted to cooperate to selectively move the support member along the cannula and between the first and second positions thereof upon relative rotational movement of the cannula and the support member.

6. The surgical access assembly according to claim 3 wherein the housing includes a seal disposed across the longitudinal opening.

7. The surgical access assembly according to claim 3 further including a compressible ring mounted between the cannula and the housing for maintaining the housing relative to the cannula.

8. The surgical access assembly according to claim 7 wherein the compressible ring is constructed of rubber or foam.

9. The surgical access assembly according to claim 3 wherein the support member is dimensioned and configured to securely engage the housing and in contacting relation therewith when in the first position of the support member.

10. The surgical access assembly according to claim 3 wherein the support member includes an outer rim, an inner rim and a plurality of spindles extending between the outer and inner rim.

11. A surgical access assembly which comprises:
    a cannula adapted for insertion through tissue to permit access to an underlying tissue site, the cannula defining a longitudinal axis and having a longitudinal passageway for passage of a surgical object for positioning with respect to the tissue site;
    a housing mounted to the cannula, the housing adapted for movement relative to the cannula in a direction transverse to the longitudinal axis;
    a seal disposed within the cannula and having a passage for reception of the surgical object in substantial sealed relation therewith; and
    a support member selectively positionable along the cannula with respect to the longitudinal axis, the support member being adapted for rotational movement relative to the housing between a first position corresponding to a secured position of the housing with respect to the cannula whereby the housing is prevented from moving in the direction transverse to the longitudinal axis, and a second position corresponding to a release position of the housing with respect to the cannula whereby the housing is permitted to move in the direction transverse to the longitudinal axis.

12. A surgical access assembly, which comprises:
- a cannula adapted for insertion through tissue to permit access to an underlying tissue site, the cannula defining a longitudinal axis and having a longitudinal passageway for passage of a surgical object for positioning with respect to the tissue site;
- a housing mounted to the cannula and defining an opening therein for receiving a surgical object therethrough, the housing adapted for radial movement relative to the cannula, wherein the opening is axial aligned with the longitudinal axis of the cannula when the housing is in a first position and the opening is axial offset from the longitudinal axis when the housing is in a second position;
- a seal disposed within the cannula and having a passage for reception of the surgical object in substantial sealed relation therewith; and
- a support member mounted to the cannula and being configured and dimensioned to move relative to the housing to selectively lock the housing at either the first position or the second position.

13. The surgical access assembly according to claim 12 wherein the support member is adapted for longitudinal movement relative to the cannula.

14. The surgical access assembly according to claim 13 wherein the support member is dimensioned and configured to move relative to the housing to engage the housing to thereby selectively lock the housing in either the first position or the second position thereof.

15. The surgical access assembly according to claim 13 wherein the support member is coaxially mounted about the cannula.

16. The surgical access assembly according to claim 15 wherein the cannula and the support member include threaded portions dimensioned and adapted to cooperate to selectively move the support member along the cannula to selectively lock the housing at either the first position or the second position thereof.

* * * * *